United States Patent [19]

Bowser et al.

[11] Patent Number: 5,202,357
[45] Date of Patent: * Apr. 13, 1993

[54] SKIN TREATMENT COMPOSITION

[75] Inventors: Paul A. Bowser, Merseyside, England; Albert Froling, Vlaardingen, Netherlands; Lammert Heslinga, Maassluis, Netherlands; Udo M. T. Houtsmuller, Vlaardingen, Netherlands; Diederik H. Nugteren, Rhoon, Netherlands; Hendrik J. J. Pabon, Vlaardingen, Netherlands; Colin Prottey, Merseyside, England

[73] Assignee: Lever Brothers Company, Division of Conopco, Inc., New York, N.Y.

[ * ] Notice: The portion of the term of this patent subsequent to Aug. 21, 2007 has been disclaimed.

[21] Appl. No.: 541,993

[22] Filed: Jun. 21, 1990

Related U.S. Application Data

[63] Continuation-in-part of Ser. No. 505,005, Jun. 16, 1983, Pat. No. 4,950,688.

[30] Foreign Application Priority Data

Jun. 16, 1982 [GB] United Kingdom ............... 8217413
Jun. 16, 1982 [GB] United Kingdom ............... 8217414
Jul. 14, 1982 [GB] United Kingdom ............... 8220442

[51] Int. Cl.$^5$ .................. A61K 7/40; A61K 7/48; A61K 9/07; A61K 9/12
[52] U.S. Cl. .................. 514/847; 424/DIG. 5; 424/47; 424/59; 424/60; 424/69; 514/873; 514/887; 514/937; 514/938; 514/944; 514/949; 514/969; 536/41; 554/61; 554/63; 554/219
[58] Field of Search .................. 260/404; 514/847

[56] References Cited

U.S. PATENT DOCUMENTS 4,464,360 8/1984 Leffler et al. .................. 424/180

FOREIGN PATENT DOCUMENTS

| 41-3698 | 3/1966 | Japan | 260/404 |
|---|---|---|---|
| 41-6463 | 4/1966 | Japan | 260/404 |
| 41-13736 | 8/1966 | Japan | 260/404 |
| 42-847 | 1/1967 | Japan | 260/404 |
| 42-23924 | 1/1967 | Japan | 260/404 |
| 43-12330 | 5/1968 | Japan | 260/404 |
| 44-5364 | 3/1969 | Japan | 260/404 |
| 45-3361 | 2/1970 | Japan | 260/404 |
| 46-6614 | 2/1971 | Japan | 260/404 |
| 46-21846 | 6/1971 | Japan | 260/404 |
| 6413837 | 6/1965 | Netherlands | 260/404 |

OTHER PUBLICATIONS

Gray et al., "Biochimica et Biophysica Acta", 528 (1978) 127-137.
Sribney et al., "Journal of Biological Chemistry" (1958), vol. 233, No. 6, pp. 1315-1321.

Primary Examiner—Dale R. Ore
Attorney, Agent, or Firm—Milton L. Honig

[57] ABSTRACT

A composition suitable for topical application to human skin comprises, in addition to a suitable vehicle an active ingredient which can control skin barrier functions. The active ingredient is (a) a long chain ω-hydroxy fatty acid or a carboxy-substituted derivative, (b) an hydroxy- or epoxy-derivative of an essential fatty acid or an ester formed between (a) and (b). Certain novel compounds of structures (a), (b) and (a)(b) esters are also claimed.

7 Claims, No Drawings

SKIN TREATMENT COMPOSITION

CROSS REFERENCES

This is a continuation-in-part of Ser. No. 505,005 filed Jun. 16, 1983, now U.S. Pat. No. 4,950,688.

The invention relates to cosmetic compositions containing as an active ingredient a fatty acid or ester thereof suitable for topical application to human skin. The invention also relates to certain synthetic or purified ω-hydroxy fatty acids and esters thereof with essential fatty acids or derivatives thereof.

It is recognised that linoleic acid is a naturally occurring fatty acid which can be isolated from skin as the free acid or as part of larger molecules, the most common being phospholipids and triglycerides. Linoleic acid is known as an essential fatty acid since it cannot be synthesised in vivo by many organisms and must therefore be present in the diet.

By "essential fatty acid" is meant an all cis n-6,9 unsaturated fatty acid which is required for proper functioning of an organism, but which cannot be synthesised by that organism.

Early experiments showed that the absence of linoleic acid from a diet fed to rats resulted in a deterioration in their appearance and general health. One specific change which occurred was the development of a poor skin condition leading to impairment of the skin permeability barrier with concommitant increase in the level of trans epidermal water loss (TEWL). Topical application of linoleic acid (in the free or triglyceride form) normalised TEWL and began to restore skin condition after about 2 to 5 days.

Topically applied linoleic acid has also proved to be beneficial to essential fatty acid deficient patients who have developed their deficiency due to fat malabsorption, or parenteral fat-free feeding.

Although linoleic acid could potentially lead to the formation of prostaglandin-like material there appears to be no evidence to suggest that this occurs in the skin. It has been demonstrated that conventional prostaglandin-type inhibitors do not prevent the restoration of the skin permeability barrier when linoleic acid is topically applied. Furthermore, it has been found that columbinic acid which has the properties of linoleic acid in restoring and maintaining adequate skin condition, cannot be converted into prostaglandin-type materials. It was thus postulated that besides its conventional structural role, for example in phospholipids and triglycerides, linoleic acid must also have a unique role in maintaining or forming a water permeability barrier.

It thus became a pre-requisite that for a molecule to be involved in the permeability barrier it must (i) contain an essential fatty acid, or a derivative thereof, and (ii) be present in the epidermis.

It has recently been proposed by Gray et al in Biochemica et Biophysica Acta, 528 (1978) 127–137, that 1-(3'-O-Acyl-β-glucosyl-N-dihydroxypentatriacontadienoyl sphingosine, in which the acyl group was predominantly linoleic acid, is present in mammalian skin and may have an important function in the cell membranes, although its barrier properties were not suggested.

We have since found O-linoleoylglucosyl ceramide to be absent from the stratum lucidum and stratum corneum, but have discovered an ester, namely O-linoleoyl ceramide, and a fatty acid, namely an O-linoleoyl hydroxy fatty acid, in these layers which appear to be involved in maintaining skin barrier function.

It is apparent that these compounds belong to a family of fatty acids and esters, having the general structure (1), as defined hereinafter, which when applied topically to the skin, bring about a marked improvement in skin condition, by enhancing skin barrier function. Thus, under conditions where the skin barrier function is impaired, for example by detergent damage, or is totally lost, for example following a severe burn, both of which conditions will lead to excessive moisture loss from skin tissue, then the compositions according to the invention will find application in at least partially restoring normal barrier function by eliminating or at least reducing moisture loss.

We have also discovered that where some of these individual compounds are to be found in the skin, they do not constitute more than 10% by weight of dry matter. Accordingly, we make no claim to such compounds having a purity of less than 10%.

The invention accordingly provides a composition suitable for topical application to human skin which comprises a suitable vehicle and, as an active ingredient, at least one compound having the structure $$X-O-Y \qquad (1)$$

in which X is H—, $C_1$ to $C_{10}$ alkyl, or

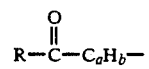

where
R is chosen from HO—, $C_1$ to $C_4$ alkoxy, polyhydroxylalkoxy, N-sphingosyl and N-(glycosylsphingosyl),
a is an integer of from 7 to 49, and
b is an integer of from 10 to 98;
and in which Y is H—, or a residue of an (n-6-cis,9-cis) unsaturated fatty acid or a residue of a derivative thereof, either residue having the structure:

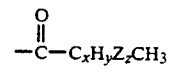

where
Z is —OH or an epoxy oxygen
x is an integer of from 16 to 20,
y is an integer of from 24 to 36, and
z is O, or an integer of from 1 to 4;
any such derivative having at least one olefinic double bond and at least one group Z located between the n-6 and n-10 position inclusive,
provided that:
when z is o
then y is an integer of from 26 to 36
or when z is an integer of from 1 to 4
then y is an integer of from 24 to 35
and provided also that:
when X is H—, or $C_1$ to $C_{10}$ alkyl,
then

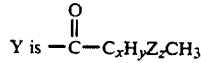

and z is an integer of from 1 to 4
and provided also that:
  when Y is —H and R is —OH, a is an integer of from 23 to 49 and b is an integer of from 42 to 98.

The active ingredient having the structure:

X—O—Y                (5)

can accordingly be a special fatty acid or a substituted fatty acid or an ester thereof.

The composition according to the invention can also comprise a mixture of these active substances.

WHERE THE ACTIVE INGREDIENT IS AN ω-HYDROXY FATTY ACID OR A SUBSTITUTED ω-HYDROXY FATTY ACID

In the above structure:

X—O—Y                (1)

where
  X is $$R-\overset{\overset{O}{\|}}{C}-C_aH_b-,$$

and
  Y is H—,
then the structure (1) becomes an ω-hydroxy fatty acid or a carboxy-substituted ω-hydroxy fatty acid thereof having the structure:

$$R-\overset{\overset{O}{\|}}{C}-C_aH_bOH \quad (2)$$

the free acid accordingly having the structure:

$$HO-\overset{\overset{O}{\|}}{C}-C_aH_bOH \quad (3)$$

When ω-hydroxy fatty acid (3) is itself to be used as active ingredient, it can have a carbon chain of from 24 to 50 carbon atoms and can contain up to two olefinic double bonds.

The ω-hydroxy fatty acid is preferably one in which the values of a are from 23 to 37, most preferably from 29 to 33 and ideally 31 to 33, and the values of b are from to 74, most preferably from 54 to 66 and ideally 58 to 66.

A preferred ω-hydroxy fatty acid having the generic structure (3) is an ω-hydroxy unsaturated fatty acid having the structure:

$$HO-\overset{\overset{O}{\|}}{C}-(CH_2)_d(CH=CH\ CH_2)_f(CH_2)_e\ OH \quad (4)$$

where
  d is an integer of from 0 to 46,
  e is an integer of from 0 to 46,
  d+e is an integer of from 20 to 46, and
  f is the integer 1 or 2,
the total carbon chain length being from 24 to 50, and containing one or two olefinic double bonds.

The preferred ω-hydroxy unsaturated fatty acid is one in which the carbon chain length is from 24 to 38, most preferably from 30 to 34 and ideally 32 to 34, and the value of f is preferably 1.

Examples of ω-hydroxy unsaturated fatty acids having the structure (4) are accordingly:

| | |
|---|---|
| ω-hydroxy-6-cis-dodecenoic acid | (5) |
| ω-hydroxy-21-cis-triacontenoic acid | (6) |
| ω-hydroxy-23-cis-triacontenoic acid | (7) |
| ω-hydroxy-23-cis-dotriacontenoic acid | (8) |
| ω-hydroxy-25-cis-dotriacontenoic acid | (9) |
| ω-hydroxy-25-cis-tetratriacontenoic acid | (10) |
| ω-hydroxy-41-cis-pentacontenoic acid | (11) |

A preferred carboxy-substituted ω-hydroxy unsaturated fatty acid having the generic structure (2) is one having the structure:

$$R-\overset{\overset{O}{\|}}{C}-(CH_2)_d(CH=CH\ CH_2)_f(CH_2)_eOH \quad (12)$$

where R is chosen from $C_1$ to $C_4$ alkoxy, polyhydroxylalkoxy, N-sphingosyl and N-(glycosylsphingosyl),
and where d, e and f have the values given for structure (4), but d & e may lie in the broader range of from 4 to 46.

The most preferred ω-hydroxy unsaturated fatty acid or carboxy-substituted ω-hydroxy unsaturated fatty acid is mono-unsaturated and can be represented as:

$$R-\overset{\overset{O}{\|}}{C}-(CH_2)_p-CH=CH-(CH_2)_qOH \quad (13)$$

where
  p is an integer of from 21 to 23, and
  q is an integer of from 6 to 8.

Examples of the carboxy-substituted ω-hydroxy unsaturated fatty acid having the structure (13) are accordingly those in which R is $C_1$ to $C_4$ alkoxy, having the structures:

$$CH_3O-\overset{\overset{O}{\|}}{C}-(CH_2)_p-CH=CH-(CH_2)_qOH \quad (14)$$

$$CH_3CH_2O-\overset{\overset{O}{\|}}{C}-(CH_2)_p-CH=CH(CH_2)_qOH \quad (15)$$

$$CH_3(CH_2)_2O-\overset{\overset{O}{\|}}{C}-(CH_2)_p-CH=CH(CH_2)_qOH \quad (16)$$

$$CH_3(CH_2)_3O-\overset{\overset{O}{\|}}{C}-(CH_2)_p-CH=CH(CH_2)_qOH \quad (17)$$

those in which R is a polyhydroxylakoxy residue, such as a substituted glycerol, having the structures:

$$\begin{array}{l}CH_2O-\overset{\overset{O}{\|}}{C}-(CH_2)_p-CH=CH(CH_2)_qOH \\ |\\ CH\ O\ A\\ |\\ CH_2O\ A\end{array} \quad (18)$$

-continued

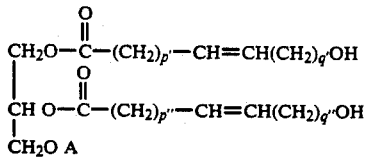  (19)

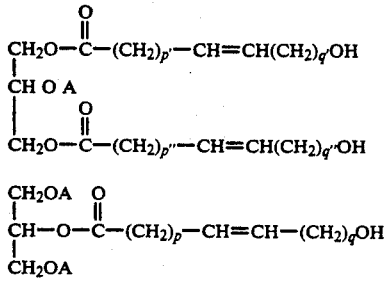  (20)

(21)

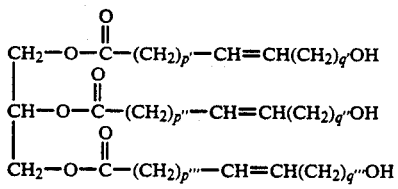  (22)

those in which R is a polyhydroxylalkoxy residue such as a substituted glycol having the structure:

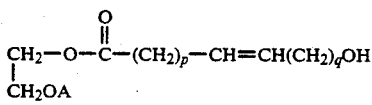  (23)

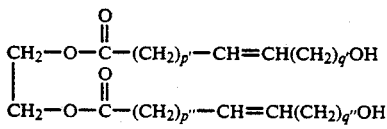  (24)

those in which R is a polyhyroxylalkoxy residue such as a substituted inositol having the structure:

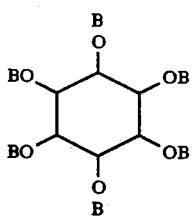  (25)

those in which R is a polyhydroxyalkoxy group such as sugar, for example glucose having the structure:

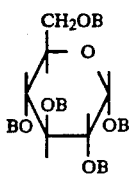  (26)

where at least one B group in structures (25) and (26) is

  (19)

and the remaining B groups are H— or $C_2$ to $C_{24}$ acyl; those in which R is a N-sphingosyl residue having the structure:

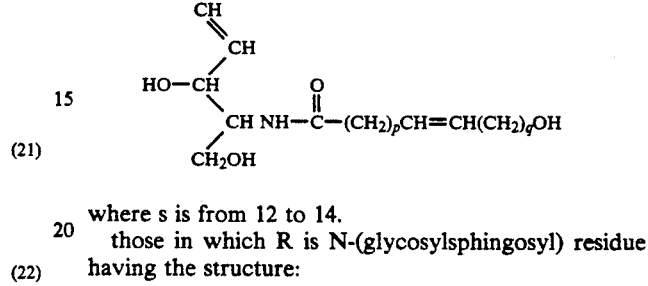  (27)

where s is from 12 to 14.

those in which R is N-(glycosylsphingosyl) residue having the structure:

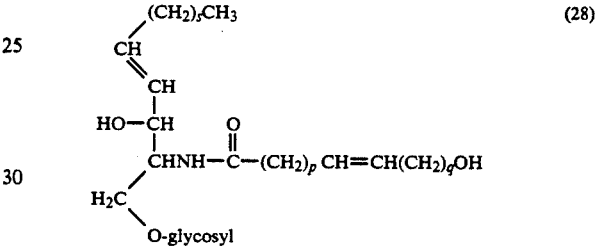  (28)

A preferred example of N-(glycosylsphingosyl)-substituted ω-hydroxy unsaturated fatty acid is where the glycosyl substituent attached to the sphingosyl residue is glucosyl.

In the above structures (19), (20), (22) and (24), p', p'' and p''', are the same or different values of p, and q', q'' and q''' are the same or different values of q.

In the above structures (18) to (21) and (23), A is H— or acyl.

WHERE THE ACTIVE INGREDIENT IS A DERIVATIVE OF AN ESSENTIAL FATTY ACID

In the above structure:

$$X-O-Y \quad (1)$$

where X is H—, or $C_1$ to $C_{10}$ alkyl
and Y is a residue of an all cis n-6,9 fatty acid or a derivative thereof having the structure:

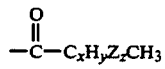

where z is an integer of from 1 to 4, then the structure (1) becomes an hydroxy or an epoxy derivative of an essential fatty acid having the structure:

  (29)

or a corresponding alkyl derivative thereof having the structure:

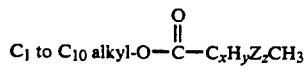
(30)

In the structure (29) where z is an integer of from to 4, that is where from 1 to 4 hydroxy or epoxy groups are present, these groups can be positioned adjacent to or in the proximity of any olefinic double bond that may be present, or indeed they can be attached to any carbon atom.

Examples of hydroxy derivatives of essential fatty acids are:

| | |
|---|---|
| 9,10,13-trihydroxy-11-octadecenoic acid | (31) |
| 9,12,13-trihydroxy-10-octadecenoic acid | (32) |
| ω-hydroxy-10,12-octadecadienoic acid | (33) |
| ω-hydroxy-9,11,-octadecadienoic acid | (34) |
| ω-hydroxy-5,8,11,13-eicosatetraenoic acid | (35) |
| 11,12,15-trihydroxy-5,8,13-eicosatrienoic acid | (36) |
| 6,7,12,13-tetrahydroxy-8,10-octadecadienoic acid | (37) |
| 12,13-oxido-10-octadecenoic acid | (38) |
| 15-hydroxy-11,12-oxido-5,8,13-eicosatrienoic acid | (39) |

WHERE THE ACTIVE INGREDIENT IS AN ESTER OF AN ω-HYDROXY FATTY ACID AND AN ESSENTIAL FATTY ACID INCLUDING SUBSTITUTED FORMS THEREOF

In the above structure:

$$X-O-Y \quad (1)$$

where X is

and Y is a residue of an all cis n-6,9 fatty acid or a derivative thereof having the structure:

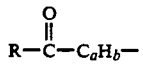

then the structure (1) becomes an ester of an ω-hydroxy fatty acid or a carboxy-substituted derivative thereof and an essential fatty acid, a hydroxy or epoxy derivative thereof having the structure:

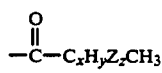
(40)

where
R is chosen from HO—, N-sphingosyl and N-(glycosylsphingosyl);
Z is —OH, or an epoxy oxygen;
a is an integer of from 7 to 49;
b is an integer of from 10 to 98;
x is an integer of from 16 to 20;
y is an integer of from 24 to 36; and
z is 0, or an integer of from 1 to 4;
the substructure

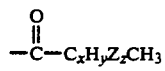

being an all -cis n-6,9 fatty acid.

The ester can comprise any of the ω-hydroxy fatty acids or carboxy-substituted ω-hydroxy fatty acids, as herein defined, condensed via the ω-hydroxy group with any of the essential fatty acid or hydroxy- or epoxy-substituted essential fatty acids as herein defined.

The respective structures of the ω-hydroxy fatty acid, including carboxy-substituents thereof, have already been defined hereinbefore, as have the respective structures of the hydroxy and epoxy derivatives of essential fatty acids.

The essential fatty acid moiety which can form part of the esters as herein defined, is an all cis n-6,9 fatty acid residue derived from essential fatty acids having from 18 to 22 carbon atoms with up to six olefinic double bonds.

Although it is preferred that the essential fatty acid moiety has two cis olefinic double bonds, for example:
octadeca-(n-6,9)-dienoic acid, (41) a particular form of which is linoleic acid, it is also possible for it to be derived from one having three or four olefinic double bonds, two of which are in the n-6,9 positions, the third or fourth being in the n-12 to n-18 positions.

Further examples of such essential fatty acids are:
octadeca-(n-6,9,12)-trienoic acid, (42) a particular form of which is γ-linolenic acid where each double bond has the cis configuration;
eicosa-(n-6,9,12)-trienoic acid, (43) a particular form of which is dihomo-γ-linolenic acid where each double bond has the cis configuration;
octadeca-(n-6,9,13)-trienoic acid, (44) a particular form of which is columbinic acid where the double bonds at the n-6 and 9 positions are in the cis configuration, and the double bond at the n-13 position is in the trans position;
eicosa-(n-6,9,13)-trienoic acid, (45) a particular form of which is an acid where the double bonds at the n-6 and n-9 positions are in the cis configuration, and the double bond at the n-13 position is in the trans position; and
eicosa-(n-6,9,12,15)-tetraenoic acid, (46) a particular form is which is arachidonic acid where each double bond is in the cis configuration.

It is also possible for the essential fatty acid moiety to be derived from one having from three to six double bonds, three of which are in the (n-3,6,9) position.

Examples of such essential fatty acids are:
octadeca-(n-3,6,9)-trienoic acid, (47) a particular form of which is α-linolenic acid where each double bond is in the cis configuration.
eicosa-(n-3,6,9,12,15)-pentaenoic acid, (48) a particular form of which is timnodonic acid where each double bond is in the cis configuration; and
docosa-(n-3,6,9,12,15,18)-hexaenoic acid, (49) a particular form of which is clupanodonic acid where each double bond is in the cis configuration.

EXAMPLES OF ESTERS ACCORDING TO THE INVENTION

An example of a preferred group of esters for use in compositions according to the invention is:

ω-(O-linoleoyl) fatty acid, or carboxy-substituted derivatives thereof, comprising from 30 to 34 carbon atoms having the structure:

$$R-\overset{O}{\underset{\|}{C}}-(CH_2)_p-CH=CH-(CH_2)_qO\ldots \quad (50)$$

$$\ldots\overset{O}{\underset{\|}{C}}(CH_2)_7\overset{cis}{(CH=CH-CH_2)_2(CH_2)_3CH_3}$$

where
p is from 21 to 23, and
q is from 6 to 8.

Specific examples of this group of esters are:
ω-(O-linoleoyl)-23-cis-dotriacontenoic acid (51) having the following identifying data:
Melting Point: 54.4° to 55.4° C.
Infra Red: Peaks found at: 3600–2500, 1695, 1425 and 950 cm$^{-1}$ (—COOH); 1728, 1255, 1210 and 1180 cm$^{-1}$ (ester); 3005 and 720 cm$^{-1}$ $$\begin{array}{c} H\;\;H \\ |\;\;\;| \\ (-C=C-) \end{array}$$

Mass Spectrometer—(Molecular Weight)
Parent peak at m/e 756;
and the structure:

$$HO-\overset{O}{\underset{\|}{C}}-(CH_2)_{21}-CH=CH-(CH_2)_8O\ldots \quad (51)$$

$$\ldots\overset{O}{\underset{\|}{C}}(CH_2)_7\overset{cis}{(CH=CHCH_2)_2(CH_2)_3CH_3}$$

ω-(O-linoleoyl)-27-cis-tetratriacontenoic acid (52), having the following identifying data:
Infra Red: Peaks found at: 3600–2500, 1695, 1425 and 950 cm$^{-1}$ (—COOH); 1728, 1255, 1210 and 1180 cm$^{-1}$ (ester); 3005 and 720 cm$^{-1}$ $$\begin{array}{c} H\;\;H \\ |\;\;\;| \\ (-C=C-) \end{array}$$

Mass Soectrometer—(Molecular Weight)
Parent peak at m/e 784;
and the structure:

$$HO-\overset{O}{\underset{\|}{C}}-(CH_2)_{25}-CH=CH-(CH_2)_6O\ldots \quad (52)$$

$$\ldots\overset{O}{\underset{\|}{C}}(CH_2)_7\overset{cis}{(CH=CHCH_2)_2(CH_2)_3CH_3}.$$

ω-(O-linoleoyl) ceramide (53), having the following identifying data:
Infra Red Peaks found at 3002 cm$^{-1}$ and absence of 970 cm$^{-1}$ indicates unsaturated-ω-hydroxy methyl ester 3350, 3300 cm$^{-1}$: secondary, amine; 1675–1680 cm$^{-1}$: carbonyl 3350, 3300 cm$^{-1}$ : secondary amine 1675–1680 cm$^{-1}$ : carbonyl(—C=O)

Mass Spectrometer (Molecular weight)
Parent peak at m/e 1023;
and the structure:

$$C_{13}H_{27}CH\overset{trans}{=}CH-\overset{OH}{\underset{|}{CH}}-\underset{CH_2OH}{\overset{|}{CH}}-NH\ldots \quad (53)$$

$$\ldots\overset{O}{\underset{\|}{C}}(CH_2)_{21}\overset{cis}{CH=CH(CH_2)_8O}\ldots$$

$$\ldots\overset{O}{\underset{\|}{C}}(CH_2)_7\overset{cis}{(CH=CHCH_2)_2(CH_2)_3CH_3}.$$

ω-(O-linoleoyl) glucosyl ceramide (54), having the following identifying data:
Infra Red: Peaks found at: 3002 cm$^{-1}$ and absence of 970 cm$^{-1}$ indicates unsaturated-ω-hydroxymethyl ester 3350, 3300 cm$^{-1}$: secondary, amine; 1675–1680 cm$^{-1}$: carbonyl 3350, 3300 cm$^{-1}$ : secondary amine 1675–1680 cm$^{-1}$ : carbonyl(—C=O)

Mass Spectrometer
Parent peak at m/e 1201;
and the structure:

$$C_{13}H_{27}CH\overset{trans}{=}CHCHCH-NH\ldots \quad (54)$$
$$\overset{|}{OH}\quad\underset{CH_2O\;Glucose}{|}$$

$$\ldots\overset{O}{\underset{\|}{C}}-(CH_2)_{21}\overset{cis}{CH=CH(CH_2)_8O}\ldots$$

$$\ldots\overset{O}{\underset{\|}{C}}-(CH_2)_7\overset{cis}{(CH=CHCH_2)_2(CH_2)_3CH_3}$$

A further example of a preferred group of esters for use as active ingredients in compositions according to the invention is that where in structure (40):
R is chosen from —OH, N-sphingosyl and N-(glycosylsphingosyl);
a is an integer of from 19 to 33,
b is an integer of from 38 to 66, and
z is 0;
and where the structure:

$$-\overset{O}{\underset{\|}{C}}-C_xH_yZ_zCH_3$$

represents an all cis n-6,9 fatty acid moiety.
Especially preferred are those wherein the active ingredient is a compound having the structure (90):

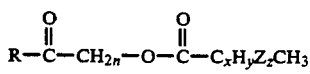 (90)

where n is an integer of from 19 to 33.

Specific examples of this group of esters are:

ω-(O-linoleoyl) fatty acid, or carboxy-substituted derivatives thereof, comprising from 19 to 33 carbon atoms, having the structure (91):

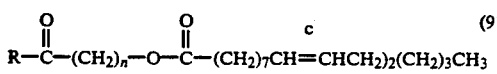 (91)

for example:

a ceramide having the structure (92):

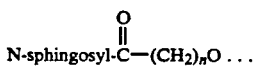 (92)

 (92)

especially ω-(O-linoleoyl) triacontanoyl sphingosine), having the structure (93):

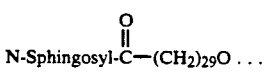 (93)

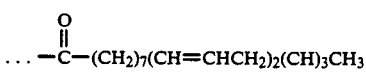

and a glycosylceramide having the structure (94):

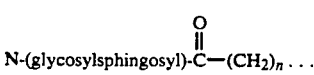 (94)

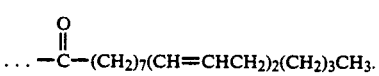

Other preferred esters include:

ω-(O-columbinoyl)-6-cis-dodecenoic acid (55), having the following identifying data: Infra Red: Peaks found at: 3600–2500, 1695, 1425 and 950 cm$^{-1}$ (—COOH); 1728, 1255, 1210 and 1180 cm$^{-1}$ (ester); 3005 and 720 cm$^{-1}$

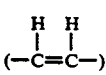

Mass Spectrometer (Molecular Weight)
Parent peak at m/e 474;
and the structure:

 (55)

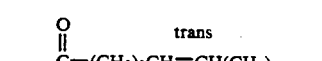

ω-(O-arachidonoyl) $C_{50}$ fatty acid having the structure:

 (56)

ω-(O-arachidonyl)-glucosyl ceramide (57), having the following identifying data:

Infra Red: Peaks found at: 3002 cm$^{-1}$ and absence of 970 cm$^{-1}$ indicates unsaturated-ω-hydroxymethyl ester 3350, 3300 cm$^{-1}$: secondary amine; 1675–1680 cm$^{-1}$: carbonyl

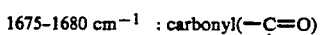

Mass Spectrometer
Parent peak at m/e 1225;
and the structure:

ω-(O-arachidonoyl) glucosyl ceramide having the structure:

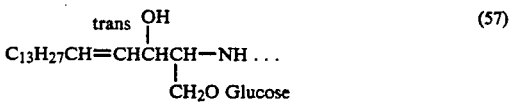 (57)

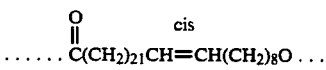

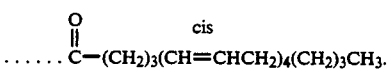

ω-(O-9,10,13-trihydroxy-11-octadecenoyl) ceramide having the structure:

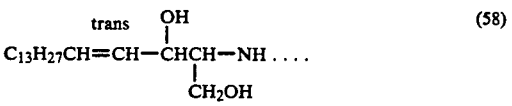 (58)

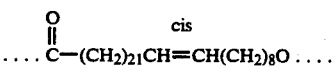

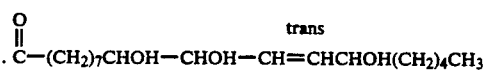

ω-(O-9-hydroxy-12,13-oxido-10-octadecenoyl)$C_{32}$ fatty acid having the structure:

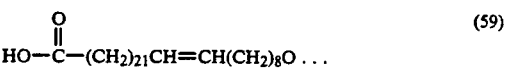 (59)

ω-(O-15-hydroxy-11,12-oxido-5,8,13-eicosatrienoyl) ceramide having the structure:

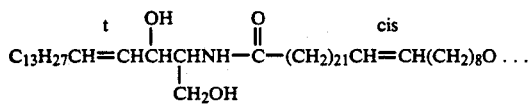

(60)

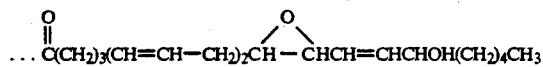

and the following identifying data:

Infra Red: Peaks found at: 3002 cm$^{-1}$ and absence of 970 cm$^1$ indicates unsaturated-ω-hydroxy methyl ester 3350, 3300 cm$^{-1}$: secondary amine; 1675–1680 cm$^{-1}$: carbonyl

Mass Spectrometer (Molecular Weight)
Parent peak at m/e 1073.

ω-(O-9,10,13-trihydroxy-11-octadecenoyl) C$_{32}$ fatty acid having the structure:

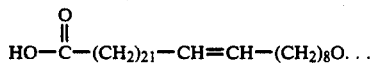

(61)

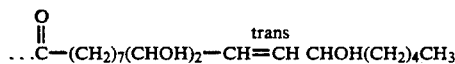

ω-(O-columbinoyl)-23-cis-dotriacontenoic acid (62), having the following identifying data:

Infra Red: Peaks found at: 3600–2500, 1695, 1425, 950 cm$^{-1}$ (—COOH); 1728, 1255, 1210 and 1180 cm-1 (ester); 3005 and 720 cm$^{-1}$

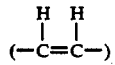

Mass Spectrometer (Molecular weight)
Parent peak at m/e 758;
and the structure:

ω-(O-Columbinoyl) C$_{32}$ fatty acid having the structure:

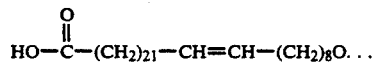
(62)

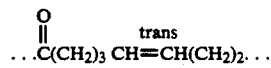

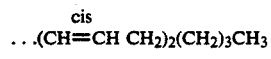

ω-(O-Columbinoyl) ceramide having the structure:

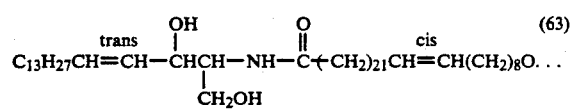
(63)

-continued

...(CH=CH CH$_2$)$_2$ (CH$_2$)$_3$ CH$_3$

ω-(O-γ-linolenoyl) C$_{32}$ fatty acid having the structure:

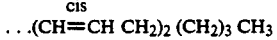
(64)

ω-(O-γ-linolenoyl) ceramide (65), having the following identifying data:

Infra Red: Peaks found at 3002 cm$^{-1}$ and absence of 970 cm$^{-1}$ indicated unsaturated-ω-hydroxy methyl ester. 3350, 3300 cm-1: secondary amine; 1675–1680 cm-1: carbonyl

Mass Spectrometer
Parent peak at m/e 1031;
and the structure;

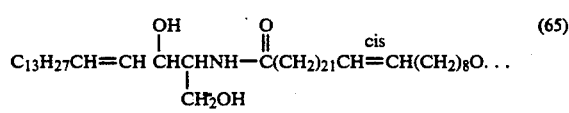
(65)

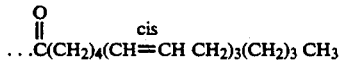

ω-(O-arachidonoyl C$_{34}$ fatty acid having the structure:

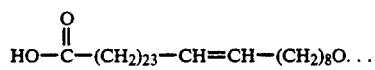
(66)

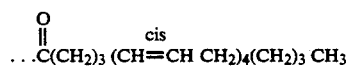

ω-(O-arachidonoyl) ceramide (67), having the following identifying data:

Infra Red: Peaks found at 3002 cm$^{-1}$ and absence of 970 cm$^{-1}$ indicated unsaturated-ω-hydroxy methyl ester. 3350, 3300 cm$^{-1}$: secondary amine; 1675–1680 cm$^{-1}$: carbonyl

Mass Spectrometer
Parent peak at m/e 1156;
having the structure:

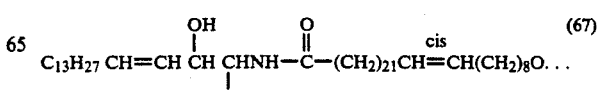
(67)

-continued

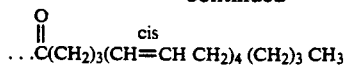

ethyl-9,10,13-trihydroxy-11-octadecenoate having the structure:

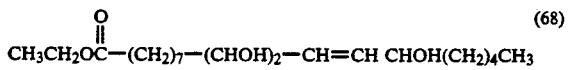
(68)

The amount of the active ingredient or mixture thereof incorporated together with a suitable vehicle into compositions for topical use can vary widely, but in general an amount of the active ingredient of from 0.0001 to 5%, preferably from 0.01 to 0.1% by weight of the composition, will provide an adequate skin benefit dose following topical application to the skin

THE VEHICLE

The composition should also comprise a vehicle to enable the active ingredient to be conveyed to the skin in an appropriate dilution.

The selection of a vehicle for the active ingredient in compositions cf the invention presents a wide range of possibilities depending on the required product form of the composition Suitable vehicles can be classified as described hereinafter.

It should be explained that vehicles are substances which can act as diluents, dispersants, or solvents for the active ingredients and which therefore ensure that they can be applied to and distributed evenly over the skin at an appropriate concentration; the vehicle is preferably one which can aid penetration of the active ingredient into the skin, thus ensuring that the effectiveness of the active ingredient is prolonged because of improved substantivity. Compositions according to this invention can include water as a vehicle, and/or at least one cosmetically acceptable vehicle other than water.

Vehicles other than water that can be used in compositions according to the invention can include solids or liquids such as emollients, propellants, solvents, humectants, thickeners and powders. Examples of each of these types of vehicles, which can be used singly or as mixtures of one or more carriers, are as follows:

Emollients, such as stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polyethylene glycol, triethylene glycol, lanolin, castor oil, acetylated lanolin alcohols, petroleum, mineral oil, butyl myristate, isostearic acid, palmitic acid, isopropyl linoleate, lauryl lactate, myristyl lactate, decyl oleate, myristyl, myristate;

Propellants, such as trichlorofluoromethane, dichlorodifluoromethane, dichlorotetrafluorethane, monochlorodifluoromethane, trichlorotrifluorethane, propane, butane, isobutane, dimethyl ether, carbon dioxide, nitrous oxide;

Solvents, such as ethyl alcohol, methylene chloride, isopropanol, castor oil, ethylene glycol monoethyl ether, diethylene glycol monobutyl ether, diethylene glycol monoethyl ether, dimethyl sulphoxide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The amount of vehicle in the composition, including water if present, should preferably be sufficient to carry at least a portion of the active ingredient to the skin in an amount which is sufficient effectively to provide skin benefit. The amount of the vehicle can comprise the major portion of the composition, particularly where little or no other ingredients are present in the composition.

The composition will accordingly comprise from 15 to 99.9999% and preferably from 50 to 99.5% by weight of the vehicle or vehicles.

OTHER INGREDIENTS

The composition according to the invention can also optionally comprise a perfume in an amount sufficient to make the composition acceptable to the consumer and pleasant to use. Usually, the perfume, when present, will form from 0.01 to 10% by weight of the composition.

The composition according the invention can contain ingredients other than those already mentioned, depending on the form of the intended product. It is, for example, possible to include antiseptics, preservatives, antioxidants, emulsifiers, colouring agents and detergents.

The composition according to the invention can also be employed as a vehicle for a wide variety of cosmetically or pharmaceutically active ingredients, particularly ingredients which have some beneficial effect when applied to the skin.

The composition thus provides.. a means whereby such active ingredients can be diluted, dispersed, conveyed to and distributed on the skin surface at an appropriate concentration.

The invention also provides a process for the preparation of a cosmetic composition for topical application to skin which comprises mixing an active ingredient, as herein defined, with a suitable vehicle to provide a concentration of from 0.001% to 0.5%.

The compositions of the invention can be formulated as liquids, for example as a lotion or milk for use in conjunction with an applicator such as a roll-ball applicator, or a spray device such as an aerosol can containing propellant, or a container fitted with a pump to dispense the liquid product. Alternatively, the compositions of the invention can be solid or semi-solid, for example sticks, creams or gels, for use in conjunction with a suitable applicator or simply a tube, bottle or lidded jar, or as a liquid-impregnated fabric, such as a tissue wipe.

Preferably the composition is an aqueous emulsion of the ester and this can be a water-in-oil emulsion, or an oil-in-water emulsion. A particularly important composition of the invention is an aqueous fat emulsion in which the aqueous phase of the emulsion acts as a carrier.

Pharmaceutical compositions for topical application are particularly important, for skin condition is dependent on the presence of essential fatty acids. Such a composition can be liquid or plastic: liquid compositions include oils comprising the ester of the invention with or without additional carrier oil; lotions, such as a solution in a physiologically acceptable solvent of an ester of the invention in free or derivative form, for instance an aqueous solution or an aqueous emulsion of the ester; and creams and ointments, such as a plastic dispersion of the ester in free or derivative form in a suitable carrier, for instance an ointment base. Such compositions are useful in the prevention and cure of skin damage caused by contact with detergents, and in treating environmental trauma due to weathering, sunburn, burns of other types and in reducing bacterial activity on the skin. In addition, these compositions will be useful for the treatment of skin showing the symptoms of essential fatty acid deficiency, for instance due to fat malabsorption in the digestive tract, and in ichthyoses.

The invention accordingly also provides a closed container containing a cosmetic composition as herein defined.

Compositions of the invention are intended especially for topical application to human skin, in particular when the skin surface has become excessively dry, fissured, eroded or otherwise damaged.

The invention accordingly also includes a process of topical administration of the composition of the invention to human subjects suffering from or liable to suffer from essential fatty acid deficiency, and other skin disorders. The dosage rate will depend on the condition to be treated as well as the route of administration. It can be stated generally that a dosage of from 100 $\mu$g active ingredient/cm$^2$ skin to 1000 $\mu$g active ingredient/cm$^2$ skin is sufficient for the skin to retain from 10 $\mu$g active ingredient/cm$^2$ skin to 100 $\mu$g active ingredient/cm$^2$ skin, which is sufficient to provide the essential fatty acid for maintenance of skin condition. Local skin symptoms may require one or more applications of this dose.

The invention also provides a composition comprising an active ingredient as herein defined and an effective amount of a physiologically acceptable autoxidation inhibitor for the active ingredient, for example butylated p-cresol, butylated hydroquinone monomethyl ether, or a tocopherol. The inhibitor can be present in amounts of from 0.005 to 5% by weight of the active ingredient.

The invention also provides for the use of an active ingredient, as herein defined, in the topical treatment of skin disorders.

The invention is illustrated by the following examples.

EXAMPLE 1

This example illustrates a high internal phase water-in-oil emulsion containing an ester of the invention.

A high internal phase water-in-oil emulsion having the following formulation was prepared:

|  | % w/w |
| --- | --- |
| Fully hydrogenated coconut oil | 3.9 |
| $\omega$-(0-linoleoyl) substituted C$_{32}$ | 0.1 |

|  | % w/w |
| --- | --- |
| fatty acid having the structure (51) |  |
| Brij 92* | 5 |
| Bentone 38 | 0.5 |
| Preservative | 0.3 |
| MgSO$_4$ 7H$_2$O | 0.3 |
| Butylated hydroxy toluene | 0.01 |
| Perfume | qs |
| Water to | 100 |

*Brij 92 is polyoxyethylene (2) oleyl ether

EXAMPLE 2

This example also illustrates a high internal phase water-in-oil emulsion containing an ester of the invention in which the formulation of Example 1 was prepared but with the following changes:
(i) liquid paraffin replaced the fully hydrogenated coconut oil, and
(ii) the ester was $\omega$-(O-linoleoyl) ceramide having the structure (53).

EXAMPLE 3

This example also illustrates a high internal phase water-in-oil emulsion containing an ester of the invention in which the formulation of Example 1 was prepared but with the following changes:
The ester was $\omega$-(O-linoleoyl) glucosylceramide having the structure (54).

EXAMPLE 4

This example illustrates an oil-in-water cream containing an ester of the invention.

An oil-in-water cream emulsion having the following formulation was prepared:

|  | % w/w |
| --- | --- |
| Mineral oil | 4 |
| $\omega$-(0-linoleoyl) substituted C$_{34}$ fatty acid having the structure (52) | 0.1 |
| Brij 56* | 4 |
| Alfol 16RD* | 4 |
| Triethanolamine | 0.75 |
| Butane-1,3-diol | 3 |
| Xanthan gum | 0.3 |
| Preservative | 0.4 |
| Perfume | qs |
| Butylated hydroxy toluene | 0.01 |
| Water to | 100 |

*Brij 56 is cetyl alcohol POE (10)
Alfol 16RD is cetyl alcohol

EXAMPLE 5

This example also illustrates an oil-in-water emulsion containing an ester of the invention, in which the formulation of example 4 was prepared but with the following change:
the ester was an $\omega$-(O-columbinoyl) C$_{12}$ fatty acid having the structure (55).

EXAMPLE 6

This example also illustrates an oil-in-water emulsion containing an ester of the invention, in which the formulation of example 4 was prepared but with the following changes:

the ester was ω-(O-arachidonoyl) glucosyl ceramide having the structure (57).

EXAMPLE 7

This example illustrates an alcoholic lotion containing an ester of the invention.
The lotion had the following formulation:

| | % w/w |
|---|---|
| ethyl 9,10,13-trihydroxy-11-octadecenoate having the structure (68) | 0.2 |
| Ethanol | 40 |
| Perfume | qs |
| Butylated hydroxy toluene | 0.01 |
| Water to | 100 |

EXAMPLE 8

This example illustrates an alcohlolic lotion containing an ester of the invention.
The lotion had the following formulations:

| | % w/w |
|---|---|
| ω-(0-linoleoyl)triacontanoyl sphingosine, having the structure (93) | 0.2 |
| Dimethylsulphoxide | 10 |
| Ethanol | 40 |
| Antioxidant | 0.1 |
| Perfume | qs |
| Water to | 100 |

EXAMPLES 9 AND 10

The following compositions according to the invention represent lotions which can be used in the treatment of dry skin:

| | % w/w | |
|---|---|---|
| | 9 | 10 |
| ω-(0-arachidonoyl) C$_{50}$ fatty acid having the structure (56) | 1.5 | — |
| ω(0-9,10,13-trihydroxy-11-octadecenoyl) ceramide, having the structure (58) | — | 0.5 |
| Perfume | 0.1 | 0.1 |
| Hydroxyethyl cellulose | 0.4 | 0.4 |
| Absolute ethanol | 25 | 25 |
| p-methyl benzoate | 0.2 | 0.2 |
| Sterilized demineralized water to | 100 | 100 |

EXAMPLES 11 AND 12

The following compositions according to the invention represent lotions which can be used in the treatment of dry skin:

| | % w/w | |
|---|---|---|
| | 11 | 12 |
| ω-(0-9-hydroxy-12,13-oxido-10-octadecenoyl) C$_{32}$ fatty acid having the structure (59) | 0.08 | — |
| ω-(0-15-hydroxy-11,12-oxido-5,8,13-eicosatrienoyl) ceramide having the structure (60) | — | 0.15 |
| Ethanol | 10 | 10 |
| Perfume | 0.5 | 0.5 |
| Distilled water to | 100 | 100 |

EXAMPLES 13 AND 14

The following compositions according to the invention represent creams which can be used to treat skin burns:

| | % w/w | |
|---|---|---|
| | 13 | 14 |
| ω-(0-9,10,13-trihydroxy-11-octadecenoyl) C$_{32}$ fatty acid having the structure (61) | 3 | — |
| ω-(0-columbinoyl) C$_{32}$ fatty acid having the structure (62) | — | 2 |
| Cetyl alcohol | 8 | 8 |
| Mineral oil | 4 | — |
| Paraffin wax | — | 2 |
| Xanthan gum | 0.3 | 0.3 |
| Preservative | 0.4 | 0.4 |
| Perfume | qs | qs |
| Demineralized water to | 100 | 100 |

EXAMPLES 15 AND 16

The following compositions according to the invention represent lotions which can be used to treat dry skin:

| | % w/w | |
|---|---|---|
| | 15 | 16 |
| ω-(0-columbinoyl) ceramide having the structure (63) | 0.9 | — |
| ω-(0-γ-linolenoyl) C$_{32}$ fatty acid having the structure (64) | 0.1 | 1 |
| Ethanol | 45 | 45 |
| Perfume | qs | qs |
| Water to | 100 | 100 |

EXAMPLES 17, 18 AND 19

These examples illustrate compositions according to the invention which are water-in-oil high internal phase emulsions.

Each emulsion consists of 10% by volume oily phase and 90% by weight aqueous phase, having the following constitution:

| | % w/w |
|---|---|
| Oily phase | |
| Sorbitan monooleate | 20 |
| Quarternium-18 hectorite | 5 |
| Liquid paraffin | 75 |
| Aqueous phase | |
| Active ingredient* | 0.5 |
| Xanthan gum | 1 |
| Sodium chloride (1% w/w solution) | 98.2 |
| Preservative | 0.3 |
| Perfume | qs |

*active ingredients:

EXAMPLE 17

ω-(O-γ-linolenoyl) ceramide, having the structure (65).

EXAMPLE 18

ω-(O-arachidonoyl) C$_{34}$ fatty acid, having the structure (66).

EXAMPLE 19

ω-(O-arachidonoyl) ceramide, having the structure (67).

Each of the compositions described in each of the foregoing examples can be applied topically to skin, particularly detergent damaged skin, or skin which has suffered a burn, in order to improve the barrier function of the skin so as to reduce moisture loss and to promote healing and/or moisturisation of the damaged skin.

The invention also relates to certain novel ω-hydroxy fatty acids and derivatives thereof and to novel esters formed between such ω-hydroxy fatty acids and certain essential fatty acids or their hydroxy or epoxy derivatives thereof.

NOVEL COMPOUNDS PER SE

According to the invention there is also provided novel synthetic or purified fatty acids and fatty acid esters and derivatives thereof having a purity of at least 10% by weight and having the structure:

$$X-O-Y \quad (1)$$

where X is an unsaturated ω-hydroxy fatty acid residue expressed as:

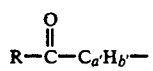

where
- $a'$ is an integer of from 27 to 33
- $b'$ is an integer of from 50 to 64, and
- R is chosen from HO—, $C_1$ to $C_4$ alkoxy, polyhydroxylalkoxy, N-sphingosyl, and N-(glycosylsphingosyl);

and where Y is —H, or a residue of an (n-6-cis, 9-cis) unsaturated fatty acid or a residue of a derivative thereof, either residue having the structure:

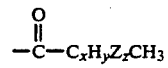

where
- Z is —OH or an epoxy oxygen
- x is an integer of from 16 to 20
- y is an integer of from 24 to 36, and
- z is 0 or an integer of from 1 to 4 any such derivative having at least one olefinic double bond and at least one group Z located between the n-6 and n-10 positions inclusive.

NOVEL COMPOUNDS: ω-HYDROXY ACIDS

In the above structure:

$$X-O-Y \quad (1)$$

where
X is

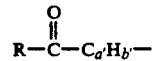

and R is HO—, or $C_1$ to $C_4$ alkoxy
and Y is H— then the structure (1) becomes an ω-hydroxy fatty acid having the structure:

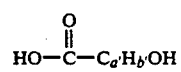

The ω-hydroxy fatty acid (69) can accordingly have a carbon chain of from 28 to 34 carbon atoms and can contain one or two olefinic double bonds and preferably has the structure:

$$HO-\overset{O}{\underset{\|}{C}}-(CH_2)_{d'}\ (CH=CH\ CH_2)_f (CH_2)_{e'}OH \quad (70)$$

where
- $d'$ is an integer of from 0 to 30
- $e'$ is an integer of from 0 to 30
- $d'+e'$ is an integer of from 24 to 30
- f is the integer 1 or 2

Most preferably, f has the value of 1, and the fatty acid is a mono unsaturated ω-hydroxy fatty acid having the structure:

$$HO-\overset{O}{\underset{\|}{C}}-(CH_2)_p-CH=CH-(CH_2)_qOH \quad (88)$$

where
- p is from 21 to 23, and
- q is from 6 to 8

Examples of ω-hydroxy unsaturated fatty acids having the structure (5) are accordingly:

| | |
|---|---|
| ω-hydroxy-21-cis-triacontenoic acid | (6) |
| ω-hydroxy-23-cis-triacontenoic acid | (7) |
| ω-hydroxy-23-cis-dotriacontenoic acid | (8) |
| ω-hydroxy-25-cis-dotriacontenoic acid | (9) |
| ω-hydroxy-25-cis-tetratriacontenoic acid | (10) |

NOVEL COMPOUNDS: SUBSTITUTED ω-HYDROXY ACIDS

In the above structure:

$$X-O-Y \quad (1)$$

where X is

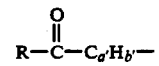

and R is chosen from polyhydroxylalkoxy, N-sphingosyl and N-(glycosylsphingosyl),
and Y is H—
then the structure (1) becomes a carboxy-substituted ω-hydroxy fatty acid having the structure:

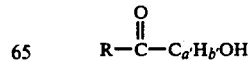

where
$a'$ is an integer of from 27 to 33, and b' is an integer of from 50 to 64.

A particularly preferred carboxy-substituted ω-hydroxy fatty acid is a carboxy-substituted ω-hydroxy unsaturated fatty acid having the structure:

$$R-\overset{O}{\underset{\|}{C}}-(CH_2)_{d'}(CH=CH\ CH_2)_{f'}(CH_2)_{e'}OH \qquad (13)$$

where
- d' is an integer of from 0 to 30
- e' is an integer of from 0 to 30
- d'+e' is an integer of from 24 to 30, and the total carbon chain length being from 8 to 50, and containing one or two olefinic double bonds.

Preferred examples of the carboxy-substituted ω-hydroxy unsaturated fatty acid are accordingly:

those in which R is $C_1$ to $C_4$ alkoxy, having the structure (14),(15),(16) or (17);

those in which R is a polyhydroxylalkoxy residue, such as a substituted glycerol, having the structure (18), (19), (20), (21) or (22);

those in which R is a polyhydroxylalkoxy residue, such as a substituted glycol, having the structure (23) or (24);

those in which R is a polyhydroxylalkoxy residue such as a substituted inositol, having the structure (25);

those in which R is a polyhydroxyalkoxy residue such as a sugar, for example glucose, having the structure (26);

those in which R is a N-sphingosyl residue having the structure (27); and those in which R is a N-(glucosylsphingosyl) residue having the structure (28).

NOVEL COMPOUNDS: ESTERS OF ω-HYDROXY FATTY ACID & ESSENTIAL FATTY ACID, INCLUDING SUBSTITUTED FORMS THEREOF

In the above structure:

$$X-O-Y \qquad (1)$$

where X is $$R-\overset{O}{\underset{\|}{C}}-C_aH_b-$$

and Y is a residue of an all cis n-6,9, fatty acid or a derivative thereof having the structure:

$$-\overset{O}{\underset{\|}{C}}-C_xH_yZ_zCH_3$$

then the structure (1) becomes an ester of an ω-hydroxy fatty acid or a carboxy substituted derivative thereof and an essential fatty acid, a hydroxy or an epoxy derivative thereof having the structure (40).

Examples of particularly preferred novel esters are those given hereinbefore by the generic structure (50).

Specific particularly preferred examples are those given hereinbefore by the specific structures: (51) to (68).

SYNTHESIS OF NOVEL ω-HYDROXY UNSATURATED FATTY ACIDS AND SUBSTITUTED ACIDS THEREOF

The ω-hydroxy unsaturated fatty acid according to the invention can be obtained by total synthesis using standard methods for poly-unsaturated fatty acid synthesis such as acetylenic coupling reactions followed by selective semi-hydrogenation.

An ω-hydroxy fatty acid, according to the invention, can be prepared from an ω-ethylenically unsaturated fatty acid having for example from 8 to 12 carbon atoms in the molecule as a starting material which is then brominated (by addition of one molecule of $Br_2$ to the double bond) and subsequently dehydrobrominated to form the corresponding ω-acetylenically unsaturated fatty acid. This unsaturated acid can then be brominated using potassium hypobromite to form the corresponding ω-acetylenically unsaturated fatty acid in which the acidic hydrogen of the acetylenic group is exchanged for bromine. Also, the ω-acetylenically unsaturated fatty acid can be treated with lithium aluminium hydride to form the corresponding ω-acetylenically unsaturated fatty alcohol.

By a Cadiot-Chodkiewicz coupling reaction, the bromide and alcohol derived from the ω-acetylenically unsaturated fatty acid can be condensed together to form a diacetylenically unsaturated ω-hydroxycarboxylic acid having a carbon chain length of from 16 to 24 carbon atoms, and this on reduction gives the corresponding ω-hydroxy saturated fatty acid.

A further condensation can be carried out to increase the chain length by reaction between the bromo- or O-tosyl derivative of this $C_{16}$ to $C_{24}$ ω-hydroxy saturated fatty acid and a further molecule of the above $C_8$ to $C_{12}$ ω-acetylenically unsaturated fatty alcohol, but with the terminal hydrogen and hydroxyl group suitably protected. Partial hydrogenation of the condensate, now containing from 24 to 36 carbon atoms, will reduce the acetylenic bond to an olefinic bond to yield the desired ω-hydroxy mono unsaturated fatty acid.

By way of example, the synthesis of a preferred ω-hydroxy unsaturated fatty acid and derivatives thereof according to the invention will now be described.

Synthesis of ω-hydroxy-23-cis-dotriacontenoic acid

The starting material in the synthesis of this ω-hydroxy $C_{32}$ mono unsaturated acid can be the ω-ethylenically $C_{11}$ unsaturated fatty acid which is first brominated and then dehydrobrominated as described earlier to form the corresponding ω-acetylenically unsaturated fatty acid according to the following scheme:

$$H_2C=CH(CH_2)_8COOH \qquad (71)$$

$$\downarrow \begin{array}{l}(a) + Br_2\\(b) - 2\ HBr\end{array}$$

$$HC\equiv C(CH_2)_8COOH \qquad (72)$$

The acid (72) is then treated in two ways. Firstly, it is brominated with potassium hypobromite to form the corresponding bromide derivative having the structure:

$$HOOC(CH_2)_8C\equiv CBr \qquad (73)$$

Secondly, the acid (72) is converted to the corresponding ω-hydroxy substituted acetylene compound using lithium aluminium hydride, this compound having the structure:

$$HC \equiv C(CH_2)_9OH \quad (74)$$

A Cadiot-Chodkiewicz coupling reaction is then carried out between the acid (73) and the ω-hydroxy acetylene compound (74) to yield a diacetylenically unsaturated ω-hydroxy carboxylic acid having the structure:

$$HOOC(CH_2)_8C \equiv C-C \equiv C(CH_2)_9OH \quad (75)$$

Complete hydrogenation of the di-acetylenically substituted compound (75) yields the ω-hydroxy fatty acid $$HOOC(CH_2)_{21}OH \quad (76)$$

Further reaction with 4-toluene sulphonyl chloride yields the toxyl derivative of the acid (76) which can e expressed as $$HOOC(CH_2)_{21}O\,Tos \quad (77)$$

and condensation of the tosyl derivative (77) with lithium substituted ω-hydroxy acetylene compound where the ω-hydroxyl group is suitably protected (78)

$$LiC \equiv C-(CH_2)_8-OTHP \quad (78)$$

will yield, after deprotection, an acetylenically unsaturated $C_{32}$ ω-hydroxy fatty acid according to the following scheme:

$$HOOC(CH_2)_{21}-O-Tos + Li\,C \equiv C(CH_2)_8-O-THP \quad (79)$$

$$\downarrow$$

$$HOOC(CH_2)_{21}C \equiv C(CH_2)_8OH$$

Partial hydrogenation of the ω-hydroxy fatty acid (79) using Lindlar's catalyst in ethyl acetate in the presence of pyridine, will form ω-hydroxy-23-cis-dotriacontenoic acid, having the structure:

$$HOOC(CH_2)_{21}\,CH\overset{c}{=}CH(CH_2)_8\,OH \quad (80)$$

Synthesis of N-(ω-hydroxy-23-cis dotriacontenoyl) sphingosine

The starting material for the synthesis of N-ω-hydroxy-23-cis-dotriacontenoyl) sphingosine can conveniently be benzoyl sphingosine which can be prepared according to the synthesis described in J.Org.-Chem. 46, 4393, (1981).

From benzoyl sphingosine, first the benzoyl group is removed with a base. Reaction with trimethylsilyl chloride then yields the bis trimethylsilyl ether of 0 sphingosine. The ω-hydroxy-23-cis-dotriacontenoic acid (80), synthesised by the process described herein, is first protected on its ω-hydroxy function using levulinic acid and then converted into the corresponding acylchloride having the structure (82). The acylchloride (82) and the bis trimethylsilyl ether of sphingosine (81) are condensed and then deprotection is carried out to remove the two trimethylsilyl ether groups and the levulinoyl group to yield N-(ω-hydroxy-23-cis-dotriacontenoyl) sphingosine (83) according to the following scheme:

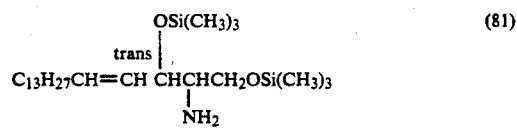

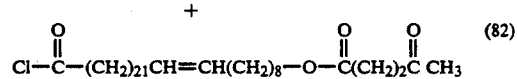

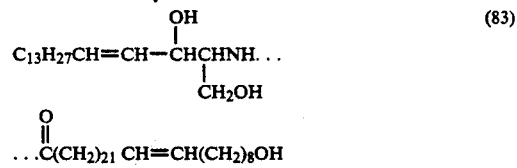

Synthesis of N-(ω-hydroxy-23-cis dotriacontenoyl) glucosylsphingosine

The starting material for the synthesis of the title compound can conveniently by 1-O-benzoyl sphingosine whose free 3-hydroxyl group is protected by reaction with tert butyl dimethyl silyl chloride (TBDMS-Cl). After removal of the benzoyl group with a base, further reaction with tetralevulinoylbromoglucose yields 3-O-tert butyl dimethyl silyl tetralevulinoyl glucosylsphingosine having the structure:

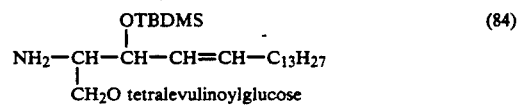

Condensation of the protected glucosylsphingosine (84) and the acylchloride (82) will yield after deprotection N-(ω-hydroxy-25-cis dotriacontenoyl) glucosylsphingosine having the structure:

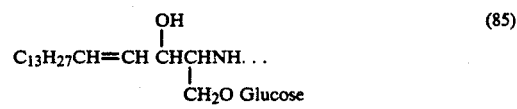

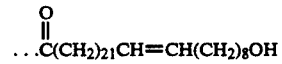

SYNTHESIS OF NOVEL ESTERS OF AN ω-HYDROXY UNSATURATED FATTY ACIDS AND ESSENTIAL FATTY ACIDS AND SUBSTITUTED ESTERS THEREOF

The esters according to the invention can be obtained by total synthesis using standard methods for polyunsaturated fatty acid synthesis such as acetylenic coupling reactions followed by selective semi-hydrogenation and condensation of the fatty acid moieties so produced to form the esters of an ω-hydroxy fatty acid and an essential fatty acid.

An ω-hydroxy fatty acid, which is subsequently condensed with an essential fatty acid to form the ester of the invention, can be prepared from an ω-ethylenically unsaturated fatty acid having for example from 8 to 12 carbon atoms in the molecule as a starting material which is then brominated (by addition of one molecule of $Br_2$ to the double bond), and subsequently dehydrobrominated to from the corresponding ω-acetylenically unsaturated fatty acid. This unsaturated acid can then be brominated using potassium hypobromite to form the corresponding ω-acetylenically unsaturated fatty acid in which the acidic hydrogen of the acetylenic group is exchanged for bromine. Also the ω-acetylenically unsaturated fatty acid can be treated with lithium aluminium hydride to form the corresponding ω-acetylenically unsaturated fatty alcohol.

By a Cadiot-Chodkiewicz coupling reaction, the bromide and alcohol derived from the ω-acetylenically unsaturated fatty acid can be condensed together to form a diacetylenically unsaturated ω-hydroxycarboxylic acid having a carbon chain length of from 16 to 24 carbon atoms, and this on reduction gives the corresponding ω-hydroxy saturated fatty acid.

A further condensation can be carried out to increase the chain length by reaction between the bromo- or O-tosyl derivative of this $C_{16}$ to $C_{24}$ ω-hydroxy saturated fatty acid and a further molecule of the above $C_8$ to $C_{12}$ ω-acetylenically unsaturated fatty alcohol, but with the terminal hydrogen and hydroxyl group suitably protected. Partial hydrogenation of the condensate, now containing from 24 to 36 carbon atoms, will reduce the acetylenic bond to an olefinic bond to yield the desired ω-hydroxy mono unsaturated fatty acid.

Condensation of the ω-hydroxy $C_{24}$ to $C_{36}$ mono unsaturated fatty acid so obtained with an essential fatty acid having from 11 to 24 carbon atoms in the molecule can be achieved by esterification, for example, with the essential fatty acid in the anhydride form.

The ester so obtained is the synthetic ester of an ω-hydroxy fatty acid and an essential fatty acid as herein defined.

By way of example, the synthesis of preferred esters and derivatives thereof according to the invention will now be described.

Synthesis of ω-(O-linoleoyl)-23-cis-dotriacontenoic acid

The starting material in the synthesis of ω-(O-linoleoyl)-23-cis-dotriacontenoic acid can be ω-hydroxy-23-cis-dotriacontenoic acid having the structure (80), which itself can be prepared according to the synthesis as described hereinbefore from the ω-ethylenically $C_{11}$ unsaturated fatty acid having the structure (71).

It is then necessary to condense the acid (80) with an excess of linoleic anhydride in the presence of a catalyst (e.g. 4-dimethylaminopyridine) to yield ω-(O-linoleoyl)-23-cis-dotriacontenoic acid, having the structure:

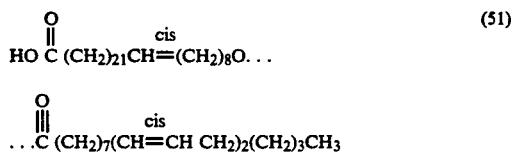

(51)

Synthesis of N-[ω-(O-linoleoyl)23-cis-dotriacontenoyl] sphingosine (53)

The starting material for the synthesis of N-[ω-(O-linoleoyl)23-cis-dotriacontenoyl] sphingosine can conveniently be 1-O-benzoyl sphingosine which can be prepared according to the synthesis described in J.Org.Chem. 46, 4393, (1981).

From 1-O-benzoyl sphingosine, first the benzoyl group is removed with base. Reaction with trimethylsilyl chloride then yields the bis trimethylsilyl ether of sphingosine. The ω-(O-linoleoyl) $c_{32}$ monoenoic acid (51), synthesised by the process described herein, is converted into the corresponding acylchloride having the structure (87). The acylchloride (87) and the bis trimethylsilyl ether of sphingosine (86) are condensed and then deprotection is carried out to remove the two trimethylsilyl ether groups to yield N-[ω-(O-linoleoyl) 23-cis-dotriacontenoyl] sphingosine according to the following scheme:

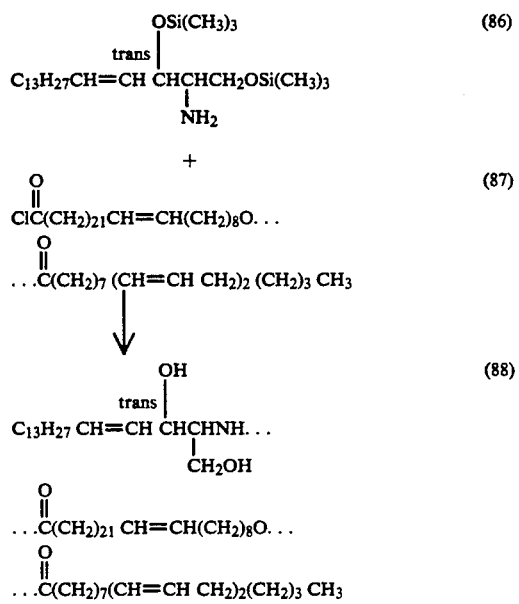

Synthesis of N-[ω-(O-linoleoyl)23-cis-dotriacontenoyl] glucosylsphingosine (54)

The starting material for the synthesis of N-[ω-(O-linoleoyl)23-cis-dotriacontenoyl] glucosylsphingosine can conveniently be 1-O-benzoyl sphingosine whose free 3-hydroxyl group is protected by reaction with tert butyl dimethyl silyl chloride. After removal of the benzoyl group with base, further reaction with tetralevulinoylbromoglucose yields 3-O-tert butyl dimethyl silyl tetralevulinoylglucosylsphingosine having the structure:

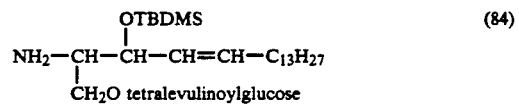

Condensation of the protected glucosyl sphingosine (84) and the acylchloride (87) will yield after deprotection N-[ω-(O-linoleoyl) 23-cis-dotriacontenoyl] glucosyl sphingosine.

Synthesis of N-[ω-(O-trihydroxylinoleoyl) 23-cisdotriacontenoyl] sphingosine (58)

N-[ω-(O-trihydroxylinoleoyl)23-cis-dotriacontenoyl] sphingosine can be synthesised from linoleic acid which is first converted enzymically to trihydroxyoctadecenoic acid and then to 9,10,13-tri-O-levulinoyl octadecen-11-oic acid. Esterification with the $C_{32}$ ω-hydroxy acid (80) and coupling with O-tert butyl dimethyl silyl sphingosine having the structure:

$$\begin{array}{c} \text{OTBDMS} \\ | \\ \text{NH}_2\text{CHCHCH}=\text{CH C}_{13}\text{H}_{27} \\ | \\ \text{CH}_2\text{OH} \end{array} \quad (89)$$

via the acyl chloride of the structure (87) followed by deprotection will yield N-[ω-(O-trihydroxylinoleoyl)23-cis-dotriacontenoyl] sphingosine,

What is claimed is:

1. A composition suitable for topical application to human skin for restoring or enhancing skin barrier function so as to eliminate or at least reduce moisture loss particularly when the skin surface has become excessively dry, fissured, eroded or otherwise damaged, which composition comprises:
   i) from 0.0001 to 5% by weight of an active ingredient; and
   ii) from 15 to 99.9999% by weight of a vehicle to act as a diluent, dispersant or solvent for the active ingredient;
   the active ingredient being an ester comprising one or more compounds having the structure:

$$\begin{array}{c} \text{O} \quad\quad\quad \text{O} \\ \| \quad\quad\quad \| \\ \text{R}-\text{C}-\text{C}_a\text{H}_b-\text{O}-\text{C}-\text{C}_x\text{H}_y\text{Z}_z\text{CH}_3 \end{array} \quad (40)$$

where
R is chosen from HO—, N-sphingosyl and N-(glycosylsphingosyl);
Z is —OH, or an epoxy oxygen;
a is an integer of from 7 to 49;
b is an integer of from 10 to 98;
x is an integer of from 16 to 20;
y is an integer of from 24 to 36; and
z is 0, or an integer of from 1 to 4;
the substructure $$\begin{array}{c} \text{O} \\ \| \\ -\text{C}-(\text{C}_x\text{H}_y\text{Z}_z)\text{CH}_3 \end{array}$$

being an all-cis n-6,9 fatty acid.

2. The composition of claim 1, wherein in the substructure of the active ingredient:
x is an integer of from 16 to 20;
y is an integer of from 26 to 36; and
z is 0.

3. The composition of claim 2, wherein the substructure of the active ingredient is derived from an essential fatty acid selected from the group consisting of:

| | |
|---|---|
| octadeca-(n-6,9)-dienoic acid | (41) |
| octadeca-(n-6,9,12)-trienoic acid | (42) |
| eicosa-(n-6,9,12)-trienoic acid | (43) |
| octadeca-(n-6,9,13)-trienoic acid | (44) |
| eicosa-(n-6,9,13)-trienoic acid | (45) |
| eicosa-(n-6,9,12,15)-tetraenoic acid | (46) |
| octadeca-(n-3,6,9)-trienoic acid | (47) |
| eicosa-(n-3,6,9,12,15)-pentaenoic acid | (48), and |
| docosa-(n-3,6,9,12,15,18)-hexaenoic acid | (49). |

4. The composition of claim 1, wherein the ester is selected from the group consisting of:

| | |
|---|---|
| ω-(O-linoleoyl)-ceramide | (53) |
| ω-(O-linoleoyl)-glucosylceramide | (54) |
| ω-(O-arachidonoyl)-glucosylceramide | (57) |
| ω-(O-9,10,13-trihydroxy-11-octadecenoyl)-ceramide | (58) |
| ω-(O-15-hydroxy-11,12-oxido-5,8,13-eicosatrienoyl)-ceramide | (60) |
| ω-(O-columbinoyl)-ceramide | (63) |
| ω-(O-γ-linolenoyl)-ceramide | (65) and |
| ω-(O-arachidonyl)-ceramide | (67). |

5. The composition of claim 1, wherein in structure (40):
a is an integer of from 19 to 33,
b is an integer of from 38 to 66, and
z is 0.

6. The composition of claim 1, wherein the ceramide is ω-(O-linolenoyl) triacontanoyl sphingosine, having the structure (93):

$$\begin{array}{c} \text{O} \\ \| \\ \text{N-sphingosyl-C}(\text{CH}_2)_{29}\text{O}\ldots \end{array} \quad (93)$$

$$\begin{array}{c} \text{O} \\ \| \\ \ldots-\text{C}-(\text{CH}_2)_7(\text{CH}=\text{CH CH}_2)_2(\text{CH}_2)_3\text{CH}_3. \end{array}$$

7. A method for restoring or enhancing human skin barrier function so as to eliminate or at least reduce moisture loss, particularly when the skin surface has become excessively dry, fissured, eroded or otherwise damaged, which method comprises the step of applying topically to the skin the composition of claim 1.

* * * * *